US007449138B2

(12) United States Patent
Shimada et al.

(10) Patent No.: US 7,449,138 B2
(45) Date of Patent: Nov. 11, 2008

(54) METHOD OF PRODUCING AERATED SOAP

(75) Inventors: Naritoshi Shimada, Tokyo (JP); Mitsuru Kunii, Tokyo (JP); Koichi Hatano, Tochigi (JP); Yasunori Miyamoto, Tochigi (JP); Manabu Shibata, Tochigi (JP); Takeshi Hasegawa, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/304,772

(22) Filed: Dec. 16, 2005

(65) Prior Publication Data

US 2006/0094611 A1 May 4, 2006

Related U.S. Application Data

(62) Division of application No. 10/130,610, filed as application No. PCT/JP01/08225 on Sep. 21, 2001, now Pat. No. 7,037,885.

(30) Foreign Application Priority Data

Sep. 22, 2000 (JP) ............................ 2000-289621

(51) Int. Cl.

| | |
|---|---|
| ***B29C 45/00*** | (2006.01) |
| ***C11D 13/16*** | (2006.01) |
| ***A61K 7/00*** | (2006.01) |

(52) U.S. Cl. .................... 264/328.1; 425/564; 425/571; 510/141; 510/145

(58) Field of Classification Search ....................... None
See application file for complete search history.

(56) References Cited

U.S. PATENT DOCUMENTS

| | | | | |
|---|---|---|---|---|
| 2,398,776 | A | 4/1946 | Bodman | |
| 3,149,188 | A | 9/1964 | Schmitt | |
| 6,800,601 | B2 * | 10/2004 | Allan et al. | 510/447 |
| 2003/0180411 | A1 | 9/2003 | Hasegawa et al. | |
| 2006/0094611 | A1 | 5/2006 | Shimada et al. | |

FOREIGN PATENT DOCUMENTS

| | | |
|---|---|---|
| JP | 4-218599 | 8/1992 |
| JP | 10-168494 | 6/1998 |
| JP | 10-195494 | 7/1998 |
| JP | 10-195495 | 7/1998 |
| JP | 11-43699 | 2/1999 |
| WO | 98/53038 | 11/1998 |

* cited by examiner

*Primary Examiner*—Necholus Ogden
(74) *Attorney, Agent, or Firm*—Oblon, Spivak, McClelland, Maier & Neustadt, P.C.

(57) ABSTRACT

In a method of producing aerated soap (5) comprising solidifying molten soap (4) having a large number of bubbles dispersed therein in a cavity (11) of a mold (1), the cavity (11) having a prescribed shape, 1.05 or more time as much molten soap (4) as the volume of the aerated soap (5) is fed to the cavity (11) and solidified in a compressed state.

14 Claims, 3 Drawing Sheets

METHOD OF PRODUCING AERATED SOAP

This application is a division of Ser. No. 10/130,610, filed Jun. 27, 2002, now Pat. No. 7,037,885.

TECHNICAL FIELD

The present invention relates to a method of producing aerated soap from aerated molten soap. More particularly, it relates to a method of producing aerated soap while preventing shrinkage or development of sink marks on cooling.

BACKGROUND ART

Applicant of the present invention has previously proposed in JP-A-10-195494 a method of producing aerated soap which comprises solidifying molten soap containing a large number of bubbles in a cavity of a mold, wherein the step of solidification is carried out in a hermetically closed cavity. The method aims at preventing development of voids or depressions in solidified soap.

According to this production method, outside air not being allowed to enter the cavity, the solidified soap hardly suffers from void or depression development. However, there still is room for further improvement for preventing soap volume reduction due to contraction of aeration gas on cooling molten soap and for preventing resultant shrinkage and/or development of sink marks.

DISCLOSURE OF THE INVENTION

Accordingly, an object of the present invention is to provide a method of producing aerated soap while preventing shrinkage and/or sink mark development on cooling in solidifying aerated molten soap.

The present invention accomplishes the above object by providing a method for producing aerated soap which comprises solidifying molten soap having a large number of bubbles dispersed therein in a mold cavity having a prescribed shape, wherein 1.05 or more times as much molten soap as the volume of aerated soap is fed to the cavity and solidified in a compressed state.

BEST MODE FOR CARRYING OUT THE INVENTION

Figures 1A, 1B, 1C:
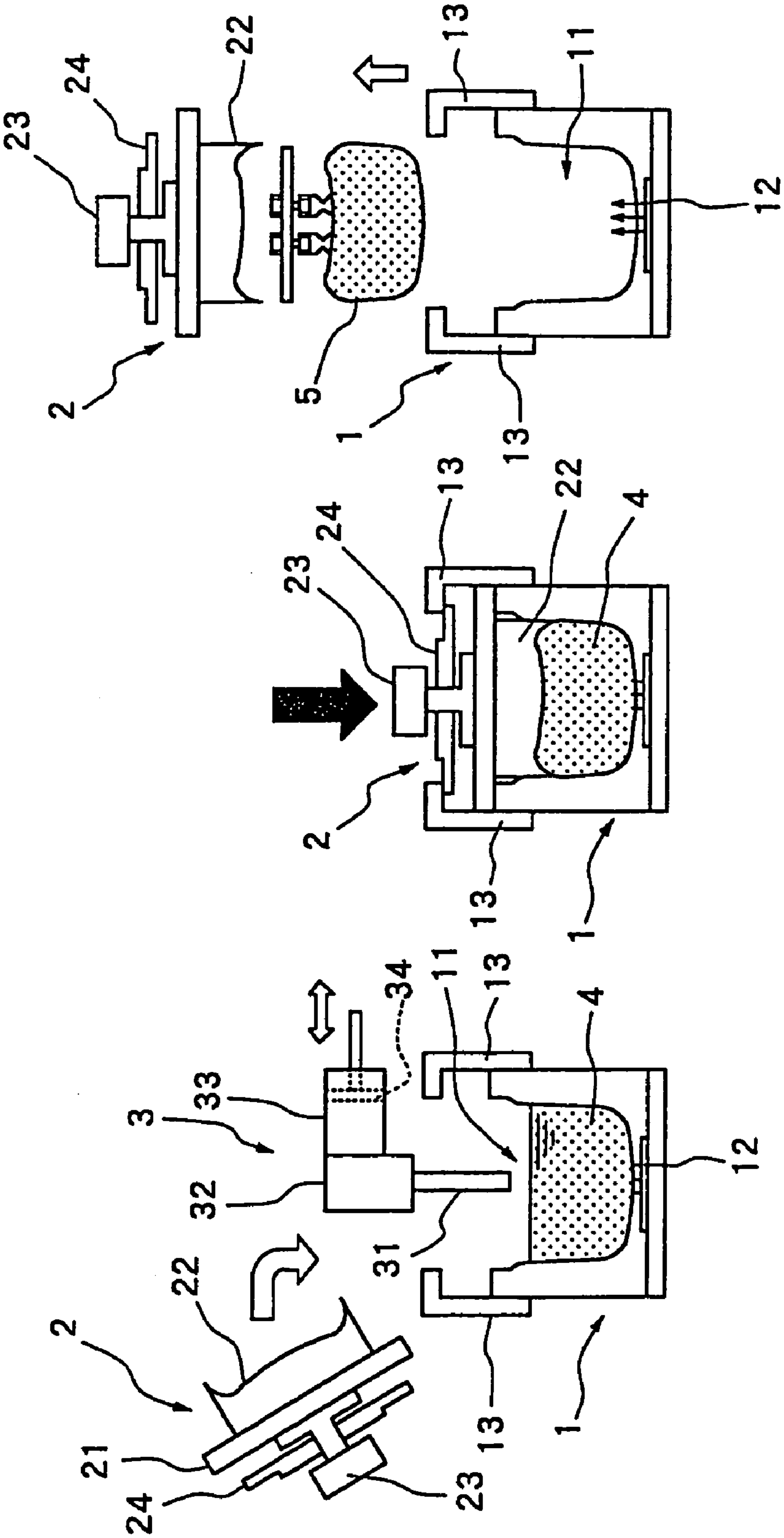
FIG. 1(*a*), FIG. 1(*b*), and FIG. 1(*c*) are sequential diagrams showing the steps involved in a first embodiment of the method for producing aerated soap according to the invention.

The present invention will be described with reference to its preferred embodiments by referring to the accompanying drawings. FIGS. 1(*a*) to (*c*) show in sequence the steps involved in the first embodiment of the production method according to the present invention.

As shown in FIG. 1(*a*), an apparatus used in this embodiment has a mold composed of a lower mold 1 and an upper mold 2 and a feeding section 3. The lower mold 1 is made of a rigid material such as metal and has a cavity 11 facing up.

The cavity 11 has a concave shape in conformity to the bottom and sides of an aerated soap as a product. A plurality of interconnecting holes 12 are made in the bottom of the cavity 11 which interconnect the cavity 11 and the outside of the lower mold 1. A clamping mechanism 13 is attached to the sides of the lower mold 1 which clamps the lower mold 1 and the upper mold 2.

The upper mold 2 is also made of a rigid material such as metal. The upper mold 2 is composed of a lid 21, a compressing part 22 which is fitted to the lower side of the lid 21 and the lower side of which is shaped to the upper contour of the aerated soap, a pressing part 23 fitted to the upper side of the lid 21, and a fitting part 24 which is fitted to the pressing part 23 with clearance and engaged with the clamping mechanism 13 of the lower mold 1.

The feeding section 3 has an injection nozzle 31, a switch valve 32, a cylinder 33, and a piston 34 disposed in the cylinder 33. The piston 34 is designed to slide back and forth in the cylinder 33. The volume of molten soap to be fed is decided by the push distance of the piston 34. Molten soap is stored in a storage tank (not shown) and circulating through a circulating duct (not shown) while passing through the storage tank. The flow of the molten soap is switched by the switch valve to feed the circulating molten soap into the cylinder 33. Separation of the molten soap into gas and liquid is prevented effectively by circulating the molten soap.

Production of aerated soap by use of an apparatus having the above-described construction will be described. Molten soap having a great number of bubbles dispersed therein is delivered to the cylinder 33 of the feeding section 3. Then, the piston 34 is pushed over a prescribed distance to push out the molten soap, whereby the molten soap 4 is fed to the cavity 11 of the lower mold 1 through the injection nozzle 31. Molten soap having a great number of bubbles dispersed therein can be prepared by, for example, the method described in JP-A-11-43699, filed by the present applicant, col. 2, line 15 to col. 5, line 1.

Various gases are useful for aerating molten soap. In particular, an inert gas, especially a non-oxidizing inert gas such as nitrogen gas, is effective to prevent the molten soap components from being oxidatively decomposed on heating to generate offensive odors, etc.

The molten soap is fed into the cavity 11 in an amount at least 1.05 time, preferably 1.1 or more time, still preferably 1.15 or more time, as much as a target volume as an aerated soap. Shrinkage and sink mark development due to cooling of the molten soap can be effectively prevented by feeding the recited volume of molten soap, assisted by the compression of the molten soap as described later. It is predictable that shrinkage or sink mark formation on cooling would hardly occur where a larger amount of molten soap than a set volume of an aerated soap is fed and compressed. The characteristic of the present invention resides in the finding that such an unpredictably small excess of volume, i.e., 1.05 or more time as much as the set volume of an aerated soap suffices to effectively prevent shrinkage or sink mark development on cooling. The upper limit of the molten soap volume to be fed is decided appropriately according to the volumetric proportion of bubbles present in the molten soap. For example, molten soap containing a relatively large proportion of bubbles will shrink to a larger degree on cooling so that the upper limit of the volume to be fed will be raised. On the other hand, where molten soap has a relatively small proportion of bubbles, the upper limit of the volume to be fed is relatively small because the degree of shrinkage on cooling will not be so high. Taking into consideration that the total volume of bubbles in the molten soap according to this embodiment is about 5 to 70%, a preferred upper limit of the volume to be fed is three times, particularly two times, the volume of aerated soap. The upper limit of the volume to be fed being three times, particularly two times, the volume of aerated soap is also preferred for preventing soap from losing its shape during the production or use on account of loss of hardness.

The volume of molten soap varies with pressure and temperature. The term "volume of molten soap" as used herein means the volume at 25° C. under atmospheric pressure.

It is preferred that the molten soap be maintained at a temperature of 55 to 80° C., particularly 60 to 70° C., when fed to the cavity 11 to prevent the molten soap from solidifying at the tip of the injection nozzle while preventing oxidation of soap and deterioration of perfume.

In this connection, the molten soap is preferably injected into the cavity 11 at a temperature higher than the melting point by 1 to 20° C., particularly 2 to 5° C., for the same reason.

It is preferred for the molten soap injected into the cavity 11 to have a viscosity of 0.001 to 50 Pa·s, particularly 0.01 to 10 Pa·s, especially 0.02 to 5 Pa·s. At a viscosity above the upper limit, injecting molten soap into the cavity 11 is difficult and needs a pump with greater output, which makes the production equipment larger. The lower limit of the viscosity practically depends on the viscosity of water contained in the molten soap. The viscosity of molten soap is measured as follows. Molten soap is poured in a cylindrical tube having an inner diameter of 10 mm and a length of 1880 mm with its downstream end open. The other end (upstream end) of the tube is provided with a pressure gage. The pressure at a shear rate of $300^{-1}$ is read, and the melt viscosity is calculated from the reading according to Hagen-Poiseuille equation. Hagen-Poiseuille equation is described, e.g., in Micheal R. Lindeburg, *Engineering Training Reference Manual* 8th Ed., pp. 17-5 to 17-6, Professional Publications, Inc., Belmont, Calif., which is incorporated herein by reference. The measuring temperature is the same as the temperature of the molten soap actually injected into the cavity.

Upon completion of feeding the molten soap 4, the upper side of the lower mold 1 is closed with the upper mold 2, and the fitting part 24 fitted to the upper mold 2 is engaged by the clamping mechanism 13 attached to the lower mold 1. Thus, the two molds are fixed. Then, as shown in FIG. 1(*b*), the pressing part fitted to the upper mold 2 is pressed down by a prescribed pressing means (not shown), such as a pressure cylinder, to compress the molten soap 4 in the cavity 11 to a set volume of an aerated soap as a product. The molten soap is let to solidify in this compressed state. These operations effectively prevent development of shrinkage and sink marks on cooling the molten soap to provide cakes of aerated soap with satisfactory appearance.

The pressure (gauge pressure) for compressing the molten soap is usually about 0.005 to 0.3 MPa, particularly about 0.05 to 0.2 MPa, while varying according to how many times as much as the set volume of an aerated soap the fed molten soap volume is.

The compression ratio of the molten soap, i.e., the compression ratio of the gaseous components in the molten soap (volume of gaseous components before compression/volume of gaseous components after compression) is preferably 1.08 to 2.5, still preferably 1.1 to 2, from the standpoint of preventing development of shrinkage or sink marks on cooling, reducing the cooling time, and improving productivity. The gaseous components in the molten soap include the gas used for aerating molten soap, steam contained in molten soap, and the like.

The solidification time of the molten soap can be shortened by cooling the lower mold 1 by a prescribed means, for example, a coolant such as water. As a matter of course, spontaneous cooling will do. Where the mold is cooled with water, the water temperature is preferably about 5 to 25° C. for preventing non-uniform dispersion of bubbles on cooling.

The molten soap is preferably solidified so that the resulting aerated soap may have an apparent density of 0.4 to 0.85 g/cm$^3$, particularly 0.6 to 0.8 g/cm$^3$. This is preferred for securing the fluidity of the molten soap, improving the cooling efficiency, improving releasability of aerated soap from the cavity 11, and improving appearance of the resulting soap. Such a solidified state can be achieved by, for example, feeding aerated molten soap made of 55 ml (under atmospheric pressure) of nitrogen gas and 90 ml of a soap composition into the cavity 11 at 64° C., compressing the aerated molten soap to 120 ml, and letting the molten soap to solidify in this compressed state. The method of measuring the apparent density of aerated soap will be described in Examples hereinafter given.

It is also preferred that the molten soap is solidified in such a manner that the proportion of bubbles (pores) having a size of 1 to 300 μm in the total pore volume in the resulting aerated soap (hereinafter referred to as a pore volume fraction) may be 80% or more for improving latherability and preventing the soap from getting sodden or swollen in contact with water. Such a solidified state can be obtained by aerating a soap composition by means of, for example, an aeration apparatus Euromix MDFO supplied by Ebara Corp. at a rotor's rotation speed of 1000 kPa (500 rpm), and solidifying the arated molten soap in the cavity by cooling while keeping the molten soap in a compressed state. The method of measuring the pore volume fraction of aerated soap will be described in Examples hereinafter given.

On completion of solidification of the molten soap, the engagement of the clamping mechanism 13 attached to the lower mold 1 and the fitting part 24 attached to the upper mold 2 is released, and the upper mold 2 is removed as shown in FIG. 1(*c*). The aerated soap 5 is taken out of the cavity 11 of the lower mold 1 by using a prescribed holding means, for example, a vacuum gripper. To facilitate removal of the aerated soap from the mold, gas such as air may be blown into the cavity 11 through the interconnecting holes 12 made in the bottom of the cavity 11.

The aerated soap thus obtained assumes a satisfactory outer appearance with neither shrinkage nor sink marks which may have developed on cooling the molten soap. Further, the bubbles inside the aerated soap are spherical. Having spherical bubbles, the soap exhibits moderate water repellency, adding improvement on conventional aerated soap having the demerit of easily getting sodden or swollen in contact with water.

Compounding components which can make up the aerated soap include fatty acid soaps, nonionic surface active agents, inorganic salts, polyols, non-soap type anionic surface active agents, free fatty acids, perfumes, and water. If desired, such additives as antimicrobials, pigments, dyes, oils, and plant extracts, can be added appropriately.

Figure 2:
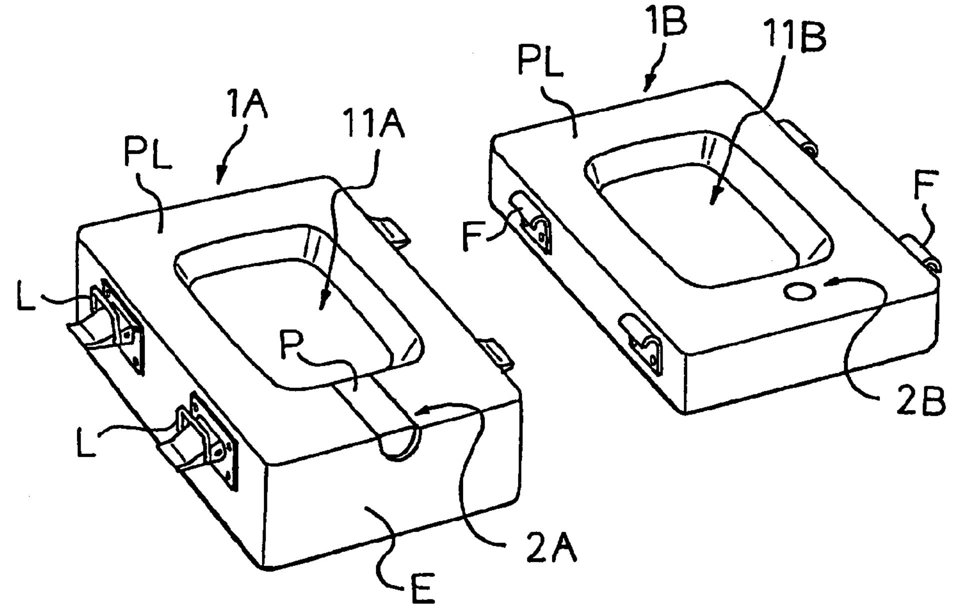
FIG. 2 is a perspective of a mold used in a second embodiment of the method for producing aerated soap according to the invention.
Figures 3A, 3B, 3C, 3D:
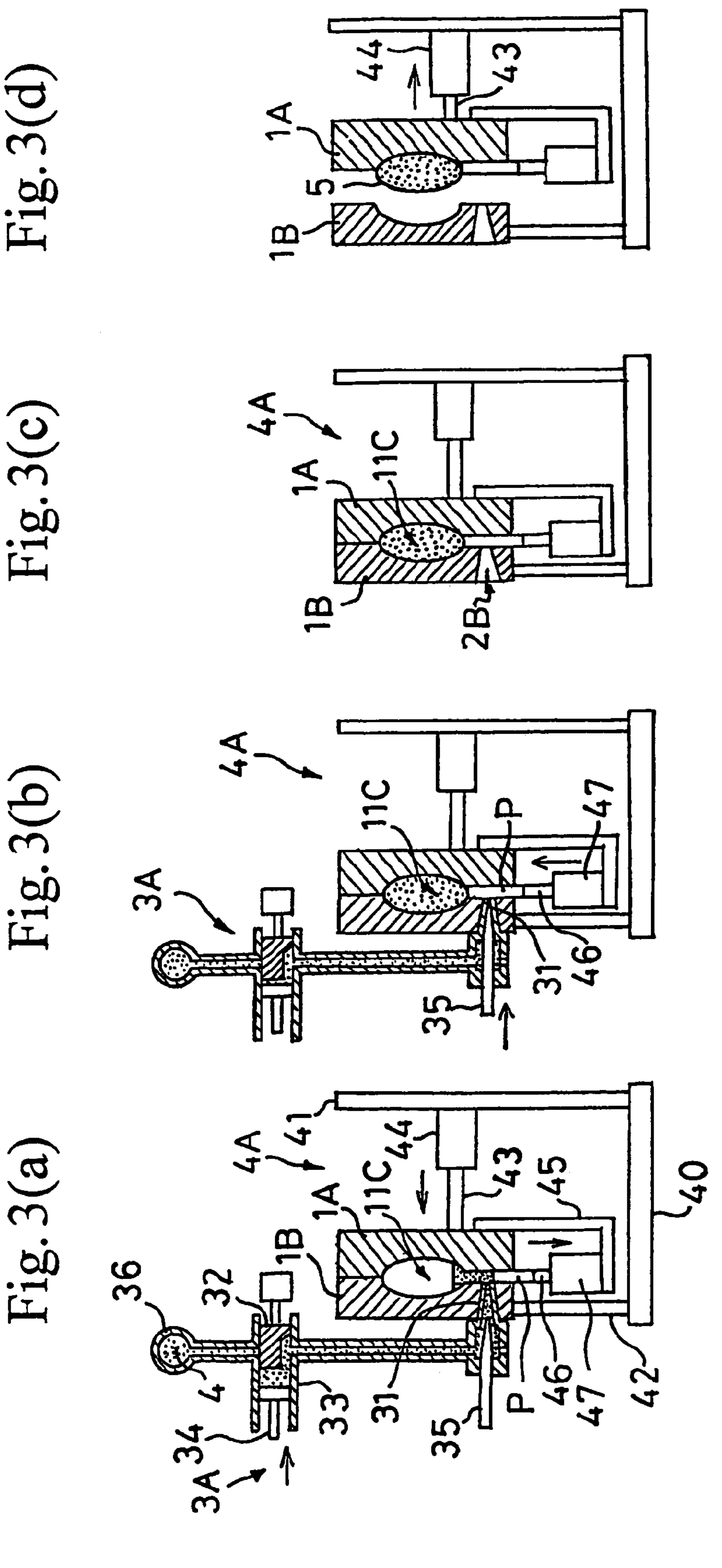
FIG. 3(*a*), FIG. 3(*b*), FIG. 3(*c*) and FIG. 3(*d*) are sequential diagrams showing the steps involved in the second embodiment of the method for producing aerated soap according to the present invention.

The second embodiment of the present invention will then be described by referring to FIGS. 2 and 3. The second embodiment will be described only with reference to differences from the first one. With reference to the particulars that are not described hereunder, the description on the first embodiment applies appropriately. In FIGS. 2 and 3 the same members as in FIG. 1 are given the same numerals used in FIG. 1.

The mold shown in FIG. 2 is a split mold made of a pair of split pieces, a first piece 1A and a second piece 1B. Each piece is made of a rigid material such as metal and has a rectangular block shape with a depression 11A or 11B in its central portion. The depressions 11A and 11B are shaped to provide a cavity (not shown) in agreement with the contour of a soap to be produced when the first piece 1A and the second piece 1B are joined together on their parting faces PL.

The second piece 1B has a nozzle insert hole 2B piercing through the outer periphery around the depression 11B in the thickness direction. The diameter of the nozzle insert hole 2B increases gradually toward the back side of the second piece 1B. The first piece 1A has a gate 2A of semicircular section engraved on part of its parting face PL. The gate 2A connects the edge side E and the depression 11A of the first piece 1A. A piston P mating the shape of the gate 2A is inserted in the gate 2A. The piston P is made of metal, plastic, etc. and designed to slide in the gate 2A. The nozzle insert hole 2B and the gate 2A are made in the respective pieces in such a configuration as to provide a tunnel connecting the nozzle insert hole 2B, the gate 2A, and the cavity when the first piece 1A and the second piece 1B are joined together on their parting faces PL. While not shown, an air vent is provided on the parting face PL of the second piece 1B. While not shown, a passageway for cooling water circulation is made in the blocks constituting the pieces 1A and 1B.

Loops L of a buckle mechanism are attached to both sides of the first piece 1A, and hooks F of the buckle mechanism are attached to both sides of the second piece 1B. The loops L and the hooks F are positioned so that they are engaged with each other with the first and the second pieces 1A and 1B joined on their parting faces PL.

The mold shown in FIG. 2 is used as fitted to the production apparatus shown in FIG. 3. The production apparatus has a mold unit 4A and a molten soap injection unit 3A. The mold is fitted above a base plate 40 of the mold unit 4A as shown in FIG. 3(*a*). The base plate 40 has an upright support plate 41 for the first piece 1A and an upright support plate 42 for the second piece 1B. The support plate 41 has fixed to the inner side thereof a cylinder 44 having a piston 43. The cylinder 44 is fixed so that the piston 43 may slide in the direction perpendicular to the support plate 41. The tip of the piston 43 is fixed to the back of the first piece 1A. Accordingly, the first piece 1A is a horizontally movable half of the mold. The first piece 1A is fitted with its gate 2A side down. An L-shaped cylinder holding member 45 is attached to the lower part of the back of the first piece 1A. The horizontal part of the cylinder holding member 45 has a cylinder 47 with a piston 46. The cylinder 47 is fitted to allow the piston 46 to slide vertically. The tip of the piston 46 is connected to the piston P disposed in the first piece 1A.

The second piece 1B is fitted to the support plate 42 with its nozzle insert hole 2B down and its depression 11B facing the depression 11A of the first piece 1A. As is understood from FIG. 3(*a*), the second piece 1B is a fixed half of the mold. The molten soap injection unit 3A is provided in the rear of the second piece 1B. The injection unit 3A comprises an injection nozzle 31, a switch valve 32, a cylinder 33, and a piston 34 disposed in the cylinder 33. The injection nozzle 31, being shaped in conformity with the shape of the nozzle insert hole 2B made in the second piece 1B, is inserted in the nozzle insert hole 2B. A gate pin 35 is provided to slide inside the injection nozzle 31. The injection of molten [resin] through the injection nozzle 31 to the cavity is controlled through push and pull of the gate pin 35. The switch valve 32 serves to connect the cylinder 33 to either a circulating duct 36 which passes through a storage tank (not shown) or the injection nozzle 31. In the state shown in FIG. 3(*a*), the cylinder 33 connects to the injection nozzle 31, with the connection between the cylinder 33 and the circulating duct 36 shut off.

The method of producing aerated soap by use of the production apparatus shown in FIG. 3 is described below. The cylinder 44 of the mold unit 4A operates to push the piston 43 forward to join the first piece 1A and the second piece 1B to close the split mold. The buckle mechanism (see FIG. 2) is fastened to clamp the split mold. Water is made to circulate through the above-mentioned cooling water passageway made in both split mold pieces. The cylinder 47 operates to draw back the piston 46, whereby part of the piston P connected to the piston 46 is drawn out of the first piece 1A. In the injection unit 3A, on the other hand, while the piston 34 is in a pushed state, the switch valve 32 operates to connect the cylinder 33 to the circulating duct 36. The piston 34 is then drawn back to deliver a predetermined amount of molten soap into the cylinder 33. The switch valve 32 then operates to cut the connection between the cylinder 33 and the circulating duct 36 and connect the cylinder 33 to the injection nozzle 31 as shown in FIG. 3(*a*). Subsequently, the piston 34 is pushed to push the molten soap 4 out of the cylinder 33. It follows that the molten soap 4 is injected under pressure into the cavity 11C through the injection nozzle 31 and the gate 2A (see FIG. 2). Similarly to the first embodiment, the volume of the molten soap to be injected is at least 1.05 time the target volume of an aerated soap. This expression does not mean that a greater amount than 1.05 time is preferred as is preferred in the first embodiment. In other words, 1.05 or more time as much molten soap as the target volume is enough. The molten soap in the cavity 11C is compressed to a set volume of an aerated soap by this operation of injection under pressure. Unlike the first embodiment, the present embodiment does not require separation of a compression step from the molten soap feeding step. That is, compression of molten soap is effected in the feeding step. Accordingly, the production method of the second embodiment achieves an increased production efficiency over that of the first embodiment. Besides, the production apparatus used in the second embodiment involves a shorter stroke in the machine movement than that used in the first embodiment, furnishing another merit that the size of the apparatus can be reduced.

Upon completion of injecting a prescribed volume of molten soap under pressure, the gate pin 35 is pushed to shut off the connection between the injection nozzle 31 and the cavity 11C as shown in FIG. 3(*b*). The cylinder 47 then operates to push the piston 46 thereby pushing the piston P connected to the piston 46 into the gate 2A (see FIG. 2). As a result, the molten soap remaining in the gate 2A is injected into the cavity 11C.

The mold unit 4A is then withdrawn (moved to the right in the drawing) whereby the injection unit 3A is separated from the second piece 1B as shown in FIG. 3(*c*), and the molten soap in the cavity 11C is cooled and solidified in the compressed state. As previously stated, the pieces 1A and 1B have been cooled to a prescribed temperature by the circulating cooling water to accelerate the cooling solidification of the molten soap in the cavity 11C. Since the molten soap has been injected under pressure in a volume 1.05 or more time the set volume of an aerated soap and compressed, shrinkage and sink mark development on cooling solidification of the molten soap are prevented.

On solidifying the molten soap, the engagement of the buckle mechanism which has been fixing the split mold pieces 1A and 1B is relieved. The cylinder 44 operates to draw back the piston 43 to separate the pieces 1A and 1B as shown in FIG. 3(*d*). The aerated soap 5 is then taken out of the cavity by a prescribed holding means (not shown).

The present invention is by no means limited to the above-described embodiments. For example, while in the first embodiment aerated soaps are produced by the use of the lower mold 1 and the upper mold 2, the lower mold 1 may be composed of a plurality of pieces according to the contour of a desired aerated soap product.

The mold used in the first and the second embodiments may be replaced with a hollow member made of a synthetic resin such as polyethylene, polypropylene, polycarbonate or polyester; a flexible thin metal plate; a flexible rubber material, etc. Such a hollow member may be used as inserted in the mold used in the second embodiment, and molten soap is fed into the hollow member and solidified in a compressed state. In this case, there is an advantage that the hollow member serves as a packaging container of the resulting aerated soap.

EXAMPLES 1 TO 4 AND COMPARATIVE EXAMPLE 1

Molten soap having a great number of bubbles dispersed therein was prepared from the compounding components shown in Table 1 below in accordance with the method described in JP-A-11-43699 Supra. Nitrogen gas was used for aeration.

TABLE 1

| Compounding Component of Molten Soap | Part by Weight |
|---|---|
| sodium laurate | 30.0 |
| sodium cocoyl isetionate | 2.0 |
| sodium lauroyl lactate | 5.0 |
| polyoxyethylene monolaurate | 2.0 |
| lauric acid | 5.0 |
| glycerol | 20.0 |
| sodium chloride | 1.5 |
| perfume | 1.5 |
| water | 32.0 |

Aerated soaps were produced from the prepared molten soap according to the steps shown in FIGS. 1(*a*) through (*c*). The molten soap was fed to the cavity 11 of the lower mold 2. The temperature and the injected volume of the molten soap were as shown in Table 2. The upper side of the lower mold 1 was closed with the upper mold 2, and the molten soap was compressed to a set volume (120 $cm^3$) by the compressing part 22 of the upper mold 2. The compression ratio of the molten soap was as shown in Table 2. In this compressed state the lower mold was cooled with cooling water at 5 to 15° C. for 3 to 15 minutes to solidify the molten soap.

On completion of solidification of the molten soap, the upper mold 2 was removed. The aerated soap was taken out of the cavity 11 by means of a vacuum gripper while blowing compressed air into the cavity 11 through the interconnecting holes 12 made through the bottom of the cavity 11. There was thus obtained an aerated soap as a final product.

The apparent density and the pore volume fraction of the resulting aerated soap were measured according to the following methods. The outer appearance of the soap was evaluated based on the following standard. The results obtained are shown in Table 2.

Measurement of Apparent Density

A rectangular parallelopiped specimen having known side lengths (e.g., 10 to 50 mm) was cut out of the resulting aerated soap and weighed. The weight was divided by the volume to give the apparent density. The volume was calculated from the three side lengths. The weight measurement was made with an electron balance. The measurement was made at 25° C.±3° C. and a relative humidity of 40 to 70%.

Measurement of Pore Volume Fraction

An aerated soap was rapidly cooled to −196° C. and cut at −150° C. The cut surface was observed in vacuo at −150° C. under an electron microscope Crio SEM JSM-5410/CRU, manufactured by JEOL Hightech Co., Ltd. The accelerating voltage was 2 kV, and a secondary electron image was used as detection signals. The diameter of pores was measured on a micrograph (magnification 500×), and a pore volume fraction was calculated from the measured diameter.

Evaluation of Appearance

The appearance was observed with the naked eye and graded according to the following standard.

A . . . Equal to the cavity shape

B . . . Substantially equal to the cavity shape

C . . . Sink marks were observed as compared with the cavity shape.

TABLE 2

| | | Example | | | | Comparative |
|---|---|---|---|---|---|---|
| | | 1 | 2 | 3 | 4 | Example 1 |
| Molten Soap | Injected Volume (%*) | 118 | 125 | 112 | 135 | 100 |
| | Temp. (° C.) | 64 | 65 | 55 | 70 | 50 |
| | Compression Ratio | 1.49 | 1.64 | 1.45 | 1.86 | 1.0 |
| Aerated Soap | Apparent Density (g/$cm^3$) | 0.64 | 0.62 | 0.75 | 0.6 | 0.85 |
| | Pore Volume Fraction (%) | 100 | 100 | 100 | 100 | 100 |
| | Appearance | A | A | B | B | C |

Note:
*Based on a set volume of an aerated soap

As is obvious from the results shown in Table 2, the aerated soaps obtained in Examples exhibit satisfactory appearance with neither shrinkage nor sink marks due to cooling. While not shown in the Table, the aerated soaps obtained in Examples gave off no offensive odor attributed to heating of the molten soap. To the contrary, the aerated soaps of Comparative Example showed partial missing or sink marks ascribed to cooling.

EXAMPLES 5 TO 7 AND COMPARATIVE EXAMPLE 2

Molten soap having a large number of bubbles dispersed therein was prepared from the same compounding components as used in Example 1 in accordance with the same procedure as in Example 1. Aerated soaps were produced from the prepared molten soap by use of the mold shown in FIG. 2 according to the steps shown in FIGS. 3(*a*) through (*d*). The temperature and the injected volume of the molten soap were as shown in Table 3. Each split mold pieces had been cooled with cooling water at 5 to 15° C. The molten soap cooling time was 3 to 15 minutes. Otherwise, the same procedures as in Example 1 were followed to obtain aerated soaps. The apparent density and the pore volume fraction of the resulting aerated soaps were measured, and the appearance of the soaps was evaluated in the same manner as in Example 1. The results obtained are shown in Table 3.

TABLE 3

| | | Example | | | Comparative |
|---|---|---|---|---|---|
| | | 5 | 6 | 7 | Example 2 |
| Molten Soap | Injected Volume (%*) | 110 | 106 | 116 | 100 |
| | Temp. (° C.) | 64 | 64 | 64 | 64 |
| | Compression Ratio | 1.41 | 1.22 | 1.59 | 0.99 |
| Aerated Soap | Apparent Density (g/cm$^3$) | 0.78 | 0.75 | 0.76 | 0.71 |
| | Pore Volume Fraction (%) | 100 | 100 | 100 | 100 |
| | Appearance | A | A | A | C |

Note:
*Based on a set volume of an aerated soap

As is apparent from the results shown in Table 3, the aerated soaps obtained in Examples exhibit satisfactory appearance with neither shrinkage nor sink marks due to cooling. While not shown in the Table, the aerated soaps obtained in Examples gave off no offensive odor attributed to heating of the molten soap. To the contrary, the aerated soaps of Comparative Example showed partial missing or sink marks ascribed to cooling. In particular as is apparent from comparison between Example 7 and Comparative Example 2, it is clearly understood that shrinkage and sink mark development on cooling can be prevented by feeding and compressing 1.05 or more time as much molten soap as the volume of the aerated soap in the cavity.

INDUSTRIAL APPLICABILITY

According to the method of the present invention for producing aerated soap, aerated molten soap can be solidified while effectively preventing shrinkage and/or sink mark development on cooling.

In particular, use of an inert gas for aerating molten soap effectively prevents generation of offensive odors attributed to heating of the molten soap.

The invention claimed is:

1. A method for producing an aerated soap product which comprises:

injecting molten soap into a mold cavity, the cavity having a shape corresponding to a shape of the aerated soap product;

plugging an injection nozzle through which the molten soap is injected into the cavity;

after plugging the injection nozzle with a gate pin, pushing molten soap remaining in a gate located between the injection nozzle and the cavity into the cavity via a cylinder that is configured to move independently of the gate pin; and solidifying molten soap having a large number of bubbles dispersed therein in the cavity having a prescribed shape in a compressed state to produce the aerated soap product, wherein a volume of molten soap fed into the cavity is 1.05 or more times as much as a volume of the aerated soap product produced, the volume of the molten soap being determined before said pushing the molten soap remaining in the gate into the cavity.

2. The method for producing an aerated soap product according to claim 1, wherein the volume of molten soap injected into the mold cavity is injected into said cavity under pressure, and said molten soap in said cavity is compressed to the volume of the aerated soap by said injection under pressure and solidified in the compressed state.

3. The method for producing an aerated soap product according to claim 1, wherein said molten soap is molten soap having been aerated with an inert gas.

4. The method for producing an aerated soap product according to claim 1, wherein said molten soap is injected into said cavity at a temperature of 55 to 80° C.

5. The method for producing an aerated soap product according to claim 1, wherein said molten soap is solidified to provide an aerated soap product having an apparent density of 0.4 to 0.85 g/cm$^3$.

6. The method for producing an aerated soap product according to claim 1, wherein said molten soap is solidified to provide an aerated soap-product containing bubbles having a size of 1 to 300 μm in a proportion of 80% or more in the total volume of bubbles.

7. A method for producing an aerated soap product, comprising:

feeding a molten soap in which a plurality of bubbles is dispersed into a mold cavity having a shape corresponding to the aerated soap product; and solidifying the molten soap in the mold cavity, wherein the feeding step includes feeding a volume of molten soap that is at least 1.05 times a volume of the aerated soap product produced;

plugging an injection nozzle through which the molten soap is fed into the cavity;

after plugging the injection nozzle with a gate pin, pushing molten soap remaining in a gate located between the injection nozzle and the cavity via a cylinder that is configured to move independently of the gate pin, wherein the volume of molten soap fed that is at least 1.05 times a volume of the aerated soap product produced is determined before the pushing.

8. The method according to claim 7, wherein the feeding step comprises feeding the molten soap under pressure.

9. The method according to claim 7, further comprising, prior to the feeding step, aerating the molten soap with an inert gas.

10. The method according to claim 7, wherein the feeding step is performed at temperatures between approximately 55° C. and approximately 80° C.

11. The method according to claim 7, wherein the aerated soap has an apparent density between approximately 0.4 g/cm$^3$ to approximately 0.85 g/cm$^3$.

12. The method according to claim 7, wherein the aerated soap includes bubbles having a size between approximately 1 μm to approximately 300 μm in a proportion of 80% or more of a total volume of bubbles.

13. The method for producing an aerated soap product according to claim 1, wherein the plugging includes moving the gate pin in a direction different than a direction of movement of the cylinder.

14. The method for producing an aerated soap product according to claim 7, wherein the plugging includes moving the gate pin in a direction different than a direction of movement of the cylinder.

* * * * *